US00PP19703P2

(12) United States Plant Patent
Westhoff

(10) Patent No.: US PP19,703 P2
(45) Date of Patent: Feb. 10, 2009

(54) ***SCAEVOLA* PLANT NAMED 'WESSCAECRYIMP'**

(50) Latin Name: *Scaevola aemula*
Varietal Denomination: Wesscaecryimp

(75) Inventor: Heinrich Westhoff, Südlohn (DE)

(73) Assignee: Gartenbau und Spezialkulturen Westhoff Gbr, Südlohn (DE)

( * ) Notice: Subject to any disclaimer, the term of this patent is extended or adjusted under 35 U.S.C. 154(b) by 0 days.

(21) Appl. No.: 12/079,311

(22) Filed: Mar. 25, 2008

(51) Int. Cl.
*A01H 5/00* (2006.01)

(52) U.S. Cl. ..... Plt./363
(58) Field of Classification Search ..... Plt./363
See application file for complete search history.

*Primary Examiner*—Annette H Para
(74) *Attorney, Agent, or Firm*—C. A. Whealy

(57) ABSTRACT

A new and distinct cultivar of *Scaevola* plant named 'Wesscaecryimp', characterized by its compact and mounded plant habit; freely branching habit with relatively short internodes; freely flowering habit; and white-colored flowers.

1 Drawing Sheet

Botanical designation: *Scaevola aemula.*
Cultivar denomination: 'WESSCAECRYIMP'

BACKGROUND OF THE INVENTION

The present invention relates to a new and distinct cultivar of *Scaevola,* botanically known as *Scaevola aemula,* and hereinafter referred to by the name 'Wesscaecryimp'.

The new *Scaevola* is a product of a planned breeding program conducted by the Inventor in Südlohn, Germany. The objective of the breeding program is to create new compact and freely-branching *Scaevola* cultivars with attractive flower coloration.

The new *Scaevola* originated from a cross-pollination made by the Inventor in Südlohn, Germany in 2003 of a proprietary selection of *Scaevola aemula* identified as code number 03P00, not patented, as the female, or seed, parent with a proprietary selection of *Scaevola aemula* identified as code number 03P10, not patented, as the male, or pollen, parent. The cultivar Wesscaecryimp was discovered and selected by the Inventor as a flowering plant within the progeny of the stated cross-pollination in a controlled environment in Südlohn, Germany in 2004.

Asexual reproduction of the new *Scaevola* by vegetative cuttings in a controlled environment in Südlohn, Germany since 2004, has shown that the unique features of this new *Scaevola* are stable and reproduced true to type in successive generations.

SUMMARY OF THE INVENTION

The cultivar Wesscaecryimp has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Wesscaecryimp'. These characteristics in combination distinguish 'Wesscaecryimp' as a new and distinct cultivar of *Scaevola:*

1. Compact and mounded plant habit.
2. Freely branching habit with relatively short internodes.

3. Freely flowering habit.
4. White-colored flowers.

Plants of the new *Scaevola* can be compared to plants of the female parent selection. Plants of the new *Scaevola* differ from plants of the female parent selection in the following characteristics:

1. Plants of the new *Scaevola* are more compact than plants of the female parent selection.
2. Plants of the new *Scaevola* have smaller leaves than plants of the female parent selection.
3. Plants of the new *Scaevola* have more compact flower clusters with smaller flowers than plants of the female parent selection.

Plants of the new *Scaevola* can be compared to plants of the male parent selection. Plants of the new *Scaevola* differ from plants of the male parent selection in the following characteristics:

1. Plants of the new *Scaevola* have finer lateral branches than plants of the male parent selection.
2. Plants of the new *Scaevola* have smaller leaves than plants of the male parent selection.
3. Plants of the new *Scaevola* have larger flowers than plants of the male parent selection.

Plants of the new *Scaevola* can be compared to plants of the *Scaevola aemula* cultivar Top Pot White, not patented. In side-by-side comparisons conducted in Südlohn, Germany, plants of the new *Scaevola* differed from plants of the cultivar Top Pot White in the following characteristics:

1. Plants of the new *Scaevola* were larger and more trailing than plants of the cultivar Top Pot White.
2. Plants of the new *Scaevola* had longer and finer lateral branches than plants of the cultivar Top Pot White.
3. Plants of the new *Scaevola* had larger leaves than plants of the cultivar Top Pot White.
4. Plants of the new *Scaevola* had larger inflorescences than plants of the cultivar Top Pot White.
5. Plants of the new *Scaevola* had larger sepals than plants of the cultivar Top Pot White.

Plants of the new *Scaevola* can also be compared to plants of the *Scaevola aemula* cultivar Fancy, disclosed in U.S.

Plant Pat. No. 9,867. In side-by-side comparisons conducted in Südlohn, Germany, plants of the new *Scaevola* differed from plants of the cultivar Fancy in the following characteristics:

1. Plants of the new *Scaevola* were more compact and mounding than plants of the cultivar Fancy.
2. Plants of the new *Scaevola* had smaller leaves than plants of the cultivar Fancy.
3. Plants of the new *Scaevola* had more compact flower clusters with smaller flowers than plants of the cultivar Fancy.
4. Plants of the new *Scaevola* and the cultivar Fancy differed in flower color as plants of the cultivar Fancy had violet blue-colored flowers.

BRIEF DESCRIPTION OF THE PHOTOGRAPHS

The accompanying colored photographs illustrate the overall appearance of the new *Scaevola,* showing the colors as true as it is reasonably possible to obtain in colored reproductions of this type. Colors in the photographs may differ slightly from the color values cited in the detailed botanical description which accurately describe the colors of the new *Scaevola.*

The photograph at the top of the sheet comprises a top perspective view of a typical flowering plants of 'Wesscaecryimp' grown in containers.

The photograph at the bottom of the sheet is a close-up view of typical flowers of 'Wesscaecryimp'.

DETAILED BOTANICAL DESCRIPTION

The aforementioned photographs and following observations, measurements and values describe plants grown in Sülohn, Germany in containers in a glass-covered greenhouse during the summer under conditions which closely approximate commercial production. During the production of the plants, day temperatures ranged from about 20° C. to 25° C. night temperatures ranged from about 16° C. to 18° C. and light levels ranged from about 3,000 lux to about 50,000 lux. Plants were about 33 weeks old when the photographs and the description were taken. In the description, color references are made to The Royal Horticultural Society Colour Chart, 2001 Edition, except where general terms of ordinary dictionary significance are used.

Botanical classification: *Scaevola aemula* cultivar Wesscaecryimp.

Parentage:

*Female, or seed parent.*—Proprietary selection of *Scaevola aemula* identified as code number 03P00, not patented.

*Male or pollen parent.*—Proprietary selection of *Scaevola aemula* identified as code number 03P10, not patented.

Propagation:

*Type.*—By vegetative cuttings.

*Time to initiate roots, summer.*—About three to four weeks at 20° C.

*Time to initiate roots, winter.*—About 23 to 30 days at 20° C.

*Time to develop roots, summer.*—About 30 to 35 days at 20° C.

*Time to develop roots, winter.*—About five weeks at 20° C.

*Root description.*—Medium in thickness, fibrous; color, 158A.

*Rooting habit.*—Freely branching; moderately dense.

Plant description:

*Plant form and growth habit.*—Compact and mounded plant habit; relatively short internodes; vigorous growth habit.

*Branching habit.*—Freely branching, about five to eight lateral branches per plant.

*Plant height.*—About 10 cm to 16 cm.

*Plant diameter* (*area of spread*).—About 35 cm to 50 cm.

Lateral branch description:

*Length.*—About 26.5 cm.

*Diameter.*—About 2 mm.

*Internode length.*—About 2.4 cm.

*Texture.*—Pubescent.

*Color.*—Close to 146B.

Foliage description:

*Arrangement.*—Alternate, simple; sessile.

*Length.*—About 4.3 cm to 6.5 cm.

*Width.*—About 2.1 cm to 2.5 cm.

*Shape.*—Ovate to elliptic.

*Apex.*—Acute.

*Base.*—Attenuate.

*Margin.*—Serrated.

*Texture, upper and lower surfaces.*—Pubescent.

*Venation pattern.*—Pinnate, arcuate.

*Color.*—Developing foliage, upper surface: Close to 147A. Developing foliage, lower surface: Close to 147B. Fully expanded foliage, upper surface: Close to 147A to 147B; venation, close to 147B. Fully expanded foliage, lower surface: Close to 147B; venation, close to 147B.

Flower description:

*Flower type and shape.*—Zygomorphic, semi-circular, fan-shaped flowers with five petals fused at the base to form a tubular flower throat; flowers sessile. Flower throat open along the upper surface exposing reproductive organs.

*Flower arrangement and quantity.*—Solitary flowers arise from leaf axils. Flowers face mostly outwardly. Freely flowering habit, typically about three to six flowers per flower cluster.

*Fragrance.*—Not detected.

*Flowering time.*—Plants flower continuously from spring to the autumn in Germany. Flowers typically last about a week on the plant. Flowers not persistent.

*Flower cluster size.*—About 14.5 cm by 5 cm.

*Flower buds.*—Shape: Lanceolate. Length: About 0.5 cm to 1.4 cm. Diameter: About 2.5 mm. Color: Close to 144A to 144B.

*Flowers.*—Length: About 1.8 cm. Width: About 2.7 cm. Flower throat diameter: About 4 mm. Flower tube length: About 1.2 cm. Flower tube diameter, base: About 2 mm.

*Petals.*—Quantity: Five, fused at base. Shape: Oblanceolate. Apex: Cuspidate. Margin: Entire. Length, above tube: About 1.3 cm. Width, above tube: About 5 mm. Texture, upper and lower surfaces: Smooth, glabrous. Color: When opening, upper and lower surfaces: Close to 155C; venation, similar to lamina. Fully opened, upper and lower surfaces: Close to 155C; venation, close to 145A to 145D. Throat: Close to N144A to N144B; venation, similar to lamina. Tube: Between N144A and 145C; venation, similar to lamina.

*Sepals.*—Quantity and arrangement: One large and two smaller sepals in a single whorl fused at the base. Length, larger sepal: About 2.5 cm. Length, smaller sepals: About 1.1 cm. Width, larger sepal: About 1.2 cm. Width, smaller sepals: About 1.7 mm Shape, larger sepal: Spatulate. Shape, smaller sepals: Acicular. Apex, all sepals: Acute. Margin, larger sepal: Indented. Margin, smaller sepals: Entire. Texture, upper and lower surfaces, all sepals: Slightly pubescent. Color, all sepals, upper surface: Close to 147A. Color, all sepals, lower surface: Close to 147B.

*Peduncle.*—Length: About 12 cm to 17 cm. Diameter: About 1.7 mm. Strength: Strong, flexible. Texture: Smooth, glabrous. Color: Close to 146B.

*Reproductive organs.*—Androecium: Stamen quantity per flower: About five. Filament length: About 3 mm to 4 mm. Filament color: Between 145D and 154D. Anther shape: Ovate. Anther length: About 1.9 mm. Anther diameter: About 1 mm. Anther color: Close to 11B. Pollen: Scarce. Pollen color: Close to 11B. Gynoecium: Pistil quantity per flower: One. Pistil length: About 1.4 cm. Style length: About 1 cm. Style color: Close to 145A to 145B; towards the apex, close to 166A. Stigma shape: Elongate. Stigma color, immature: Close to 155D; center, close to 144A. Stigma color, mature: Close to 155A; center, close to 160C. Ovary color: Close to 144A to 144B.

*Seed.*—Quantity per flower: One. Length: About 1.5 mm to 2 mm. Diameter: About 1 mm to 1.5 mm. Color: Close to 202A.

Temperature tolerance: Plants of the new *Scaevola* have been observed to tolerate temperatures from about 5° C. to about 30° C.

Pathogen/pest resistance: Plants of the new *Scaevola* have not been shown to be resistant to pathogens and pests common to *Scaevola*.

It is claimed:

1. A new and distinct *Scaevola* plant named 'Wesscaecryimp' as illustrated and described.

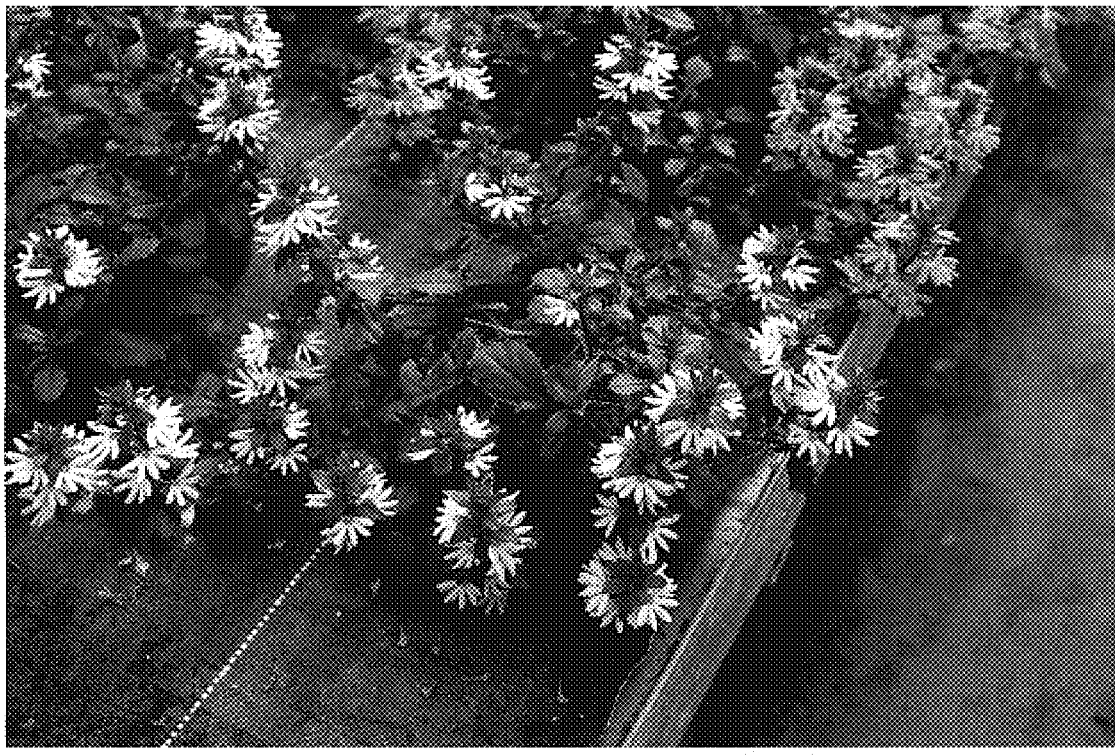
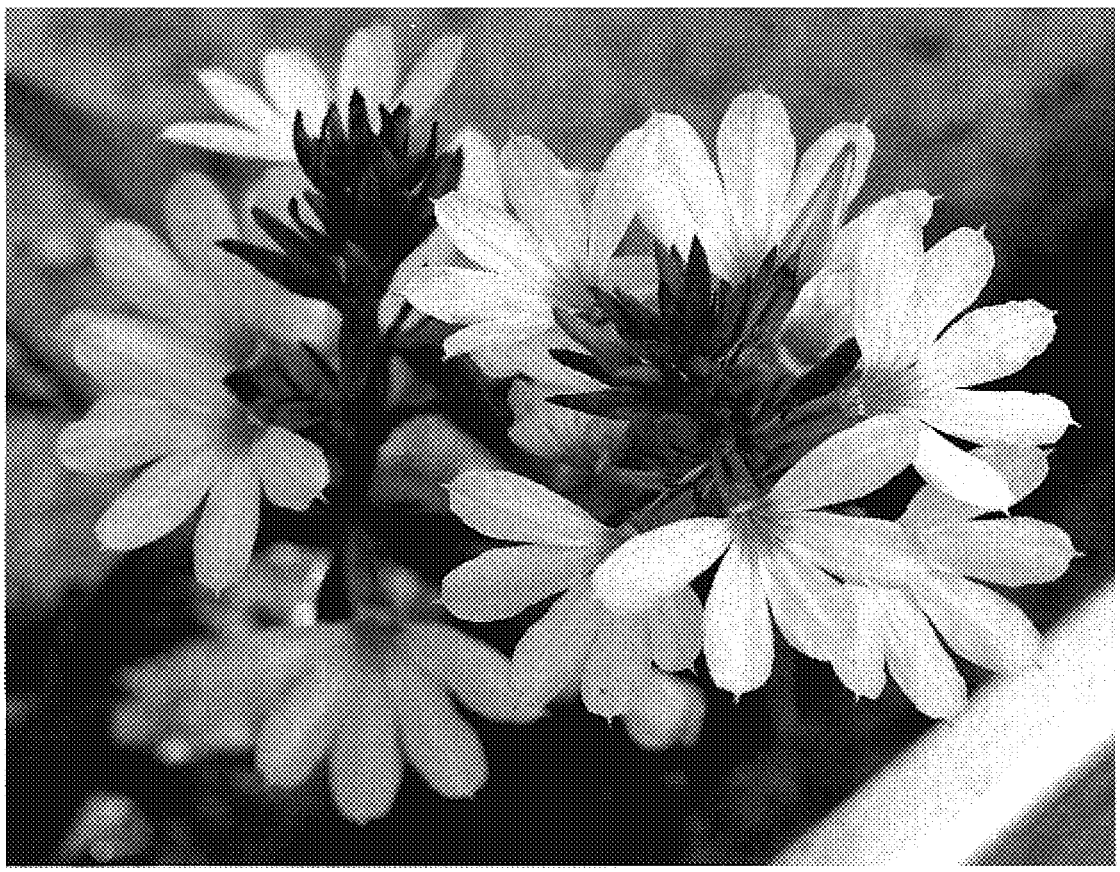

* * * * *